(12) United States Patent
Yin

(10) Patent No.: US 10,554,612 B2
(45) Date of Patent: Feb. 4, 2020

(54) INFORMATION EXCHANGE SYSTEM, METHOD, AND APPARATUS FOR MAKING MEDICAL APPOINTMENTS

(71) Applicant: Tencent Technology (Shenzhen) Company Limited, Shenzhen (CN)

(72) Inventor: Jie Yin, Shenzhen (CN)

(73) Assignee: TENCENT TECHNOLOGY (SHENZHEN) COMPANY LIMITED, Shenzhen, Guangdong Province (CN)

(*) Notice: Subject to any disclaimer, the term of this patent is extended or adjusted under 35 U.S.C. 154(b) by 189 days.

(21) Appl. No.: 15/709,839

(22) Filed: Sep. 20, 2017

(65) Prior Publication Data

US 2018/0013712 A1 Jan. 11, 2018

Related U.S. Application Data

(63) Continuation-in-part of application No. PCT/CN2016/083473, filed on May 26, 2016.

(30) Foreign Application Priority Data

Nov. 26, 2015 (CN) .......................... 2015 1 0849481

(51) Int. Cl.
```
G06Q 50/00      (2012.01)
G06Q 20/14      (2012.01)
H04L 12/58      (2006.01)
G06Q 50/22      (2018.01)
```
(52) U.S. Cl.
CPC ............ *H04L 51/32* (2013.01); *G06Q 20/14* (2013.01); *G06Q 50/01* (2013.01); *G06Q 50/22* (2013.01)

(58) Field of Classification Search
None
See application file for complete search history.

(56) References Cited

U.S. PATENT DOCUMENTS 8,423,387 B1 * 4/2013 Mirza .................. G06F 19/328
                                                          705/3

FOREIGN PATENT DOCUMENTS

| CN | 101867612 A | 10/2010 |
| CN | 101937489 A | 1/2011 |
| CN | 102117385 A | 7/2011 |

(Continued)

OTHER PUBLICATIONS

Tencent Technology, ISRWO, PCT/CN2016/083473, Aug. 4, 2016, 7 pgs.

(Continued)

*Primary Examiner* — Shirley X Zhang
(74) *Attorney, Agent, or Firm* — Morgan, Lewis & Bockius LLP

(57) ABSTRACT

A method for supporting hospital visits on a social network platform includes: detecting a user input for registering a visit at a hospital using a social network client application of the social network platform; in response to detecting the user input: obtaining a registration number for the visit, wherein the registration number indicates an ordinal position of the user in a hospital queue of multiple visitors to the hospital; and displaying a group chat interface for a group conversation including a social network identity of the user and a public social network identity of the hospital; and displaying a payment request for the visit in the group chat interface.

17 Claims, 7 Drawing Sheets

(56) References Cited

FOREIGN PATENT DOCUMENTS

| | | | |
|---|---|---|---|
| CN | 103559673 A | | 2/2014 |
| CN | 104574065 | * | 4/2015 |
| CN | 104574065 A | * | 4/2015 |
| CN | 104574065 A | | 4/2015 |
| CN | 104821032 A | | 8/2015 |
| CN | 104965977 A | | 10/2015 |
| CN | 105516258 A | | 4/2016 |

OTHER PUBLICATIONS

Tencent Technology, IPRP, PCT/CN2016/083473, May 29, 2018, 6 pgs.

* cited by examiner

| Order of payment during a hospital visit |
|---|

Order number: weixin1010212155

Patient: A

Fee item
- Western medicine fee: 0.13 RMB
- Medical test fee: 0.9 RMB
- Chinese herbal medicine fee: 0.12 RMB
- Treatment fee: 0.2 RMB Total fee    1.35 RMB

[ Confirm ]

FIG. 4

INFORMATION EXCHANGE SYSTEM, METHOD, AND APPARATUS FOR MAKING MEDICAL APPOINTMENTS

RELATED APPLICATIONS

This application is a continuation-in-part application of PCT/CN2016/083473, entitled "SYSTEM, METHOD AND DEVICE FOR INFORMATION INTERACTION" filed on May 26, 2016, which claims priority to Chinese Patent Application No. 201510849481.8, filed with the State Intellectual Property Office of the People's Republic of China on Nov. 26, 2015, and entitled "INFORMATION EXCHANGE SYSTEM, METHOD, AND APPARATUS", both of which are incorporated herein by reference in their entirety.

FIELD OF THE TECHNOLOGY

The present disclosure relates to the field of information technologies, and in particular, to an information exchange system, method, and apparatus.

BACKGROUND OF THE DISCLOSURE

With development of information technologies, a hospital information system (HIS) is more widely applied to running and management of a hospital.

In an existing hospital information system, a hospital staffer performs face-to-face interaction with a patient, so as to determine hospital visit information of the patient, manually enters the hospital visit information into a terminal device of the hospital information system, and then feeds back the hospital visit information in a form of a printed document to the patient, so that the patient performs a next operation of hospital visit based on the document. For example, in a registration process, a patient tells a hospital staffer about hospital visit information by means of filling in a hospital visit information form or oral description at a hospital service window, and pays corresponding registration fees according to the hospital visit information. After determining that the registration fees have been received, the staffer enters the hospital visit information of the patient into a terminal device of a hospital information system, and after confirming that registration is completed, feeds back the hospital visit information in a form of a printed registration form to the patient. The patient brings the registration form to a department indicated by the registration form to perform a next operation of hospital visit.

SUMMARY

Embodiments of the present technology provide an information exchange system, method, and apparatus.

According to a first aspect of the embodiments of the present technology, an information exchange system is provided, the system including a hospital server, an information exchange server, and at least one user terminal;

the hospital server including a first server and a second server; the first server being configured to generate hospital visit instruction information of a user according to hospital visit information of the user, the hospital visit instruction information being at least used for indicating a current to-be-performed hospital visit operation of the user; the second server being configured to send the hospital visit instruction information to an information exchange server, so that the information exchange server sends the hospital visit instruction information to the user terminal, to complete the hospital visit operation; the hospital visit information including at least one of a to-be-conducted hospital visit item, fee information about a to-be-conducted hospital visit item, a conducted hospital visit item, or result information about a conducted hospital visit item;

the information exchange server being configured to: receive the hospital visit instruction information, the hospital visit instruction information being at least used for indicating the current to-be-performed hospital visit operation of the user; and send the hospital visit instruction information to the user terminal based on the user identifier of the user; and the user terminal being configured to: receive the hospital visit instruction information, the hospital visit instruction information being at least used for indicating the current to-be-performed hospital visit operation of the user; and display the hospital visit instruction information on an information exchange interface that is between the user and a public social network identifier of a specified hospital.

In an embodiment of the present technology, the second server is further configured to receive registration request information of the user, where the registration request information includes at least the user identifier; and correspondingly, the first server is further configured to: receive the registration request information, and generate the hospital visit information of the user based on identity information carried in the registration request information, where the hospital visit information includes at least a to-be-conducted hospital visit item and fee information about a to-be-conducted hospital visit item; or generate the hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the first server is further configured to update the hospital visit information of the user according to an operation instruction of a hospital staffer. The hospital visit information includes at least one of a to-be-conducted hospital visit item, fee information about a to-be-conducted hospital visit item, a conducted hospital visit item, or result information about a conducted hospital visit item.

In an embodiment of the present technology, the second server is further configured to: establish a binding relationship between the hospital visit information of the user and the user identifier of the user, and invoke a hospital visit instruction information sending port according to the binding relationship, to send the hospital visit instruction information to the information exchange server in a form of a template message.

In an embodiment of the present technology, the first server is configured to: when the hospital visit information of the user includes fee information about a to-be-conducted hospital visit item, generate the hospital visit instruction information according to the fee information about a to-be-conducted hospital visit item, where the hospital visit instruction information is at least used for indicating a current to-be-performed payment operation of the user; and correspondingly, when the second server receives payment completion confirmation information, the first server updates the hospital visit information of the user according to the payment completion confirmation information.

In an embodiment of the present technology, the information exchange server is configured to: receive a payment request of the user after sending the hospital visit instruction information to the user terminal, where the payment request includes payment verification information;

perform verification on the payment request of the user according to the payment verification information, and perform a money transfer operation according to the user identifier of the user and the public identifier of the specified hospital when the verification of the payment request of the user succeeds; and send payment completion confirmation information to the hospital server when the money transfer operation is completed, so that the hospital server updates the hospital visit information of the user according to the payment completion confirmation information.

In an embodiment of the present technology, the information exchange server is configured to establish a follow relationship between the user and the public identifier of the specified hospital.

In an embodiment of the present technology, the user terminal is further configured to: send registration request information to the information exchange server according to a trigger operation performed on a registration option by the user on the information exchange interface, where the registration request information includes at least the user identifier, and the registration request information is used for enabling the hospital server to receive the registration request information, and generate hospital visit information of the user based on identity information carried in the registration request information, where the hospital visit information includes at least a to-be-conducted hospital visit item and fee information about a to-be-conducted hospital visit item, or the registration request information is used for enabling the hospital server to generate hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the user terminal is further configured to: after displaying the hospital visit instruction information on the information exchange interface that is between the user and the public identifier of the specified hospital, monitor a clicking operation performed on the indication information by the user on the information exchange interface; display a payment interface when detecting the clicking operation performed on the indication information; and complete a payment process according to an operation performed by the user on the payment interface.

According to a second aspect of the embodiments of the present technology, an information exchange method is provided, the method including:

generating hospital visit instruction information of a user according to hospital visit information of the user, the hospital visit instruction information being at least used for indicating a current to-be-performed hospital visit operation of the user; and sending the hospital visit instruction information to an information exchange server based on a user identifier of the user, so that the information exchange server sends the hospital visit instruction information to the user terminal, to complete the hospital visit operation;

the hospital visit information including at least one of a to-be-conducted hospital visit item, fee information about a to-be-conducted hospital visit item, a conducted hospital visit item, or result information about a conducted hospital visit item.

According to a third aspect of the embodiments of the present technology, an information exchange method is provided, the method including:

receiving hospital visit instruction information, the hospital visit instruction information being at least used for indicating a current to-be-performed hospital visit operation of a user; and sending the hospital visit instruction information to a user terminal based on a user identifier of the user.

According to a fourth aspect of the embodiments of the present technology, an information exchange method is provided, the method including:

receiving hospital visit instruction information, the hospital visit instruction information being at least used for indicating a current to-be-performed hospital visit operation of a user; and displaying the hospital visit instruction information on an information exchange interface that is between the user and a public social network identifier of a specified hospital.

According to a fifth aspect of the embodiments of the present technology, an information exchange apparatus is provided, the apparatus including:

a generation module, configured to generate hospital visit instruction information of a user according to hospital visit information of the user, the hospital visit instruction information being at least used for indicating a current to-be-performed hospital visit operation of the user; and a transceiver module, configured to send the hospital visit instruction information to an information exchange server based on a user identifier of the user, so that the information exchange server sends the hospital visit instruction information to the user terminal, to complete the hospital visit operation;

the hospital visit information including at least one of a to-be-conducted hospital visit item, fee information about a to-be-conducted hospital visit item, a conducted hospital visit item, or result information about a conducted hospital visit item.

According to a sixth aspect of the embodiments of the present technology, an information exchange apparatus is provided, the apparatus including:

a receiving module, configured to receive hospital visit instruction information, the hospital visit instruction information being at least used for indicating a current to-be-performed hospital visit operation of a user; and a sending module, configured to send the hospital visit instruction information to a user terminal based on a user identifier of the user.

According to a seventh aspect of the embodiments of the present technology, an information exchange apparatus is provided, the apparatus including:

a hospital visit information receiving module, configured to receive hospital visit instruction information, the hospital visit instruction information being at least used for indicating a current to-be-performed hospital visit operation of a user; and a display module, configured to display the hospital visit instruction information on an information exchange interface that is between the user and a public social network identifier of a specified hospital.

According to an eighth aspect of the embodiments of the present technology, a server is provided, including:

a processor; and a memory that is configured to store an instruction that can be executed by the processor;

the processor being configured to:

generate hospital visit instruction information of a user according to hospital visit information of the user, the hospital visit instruction information being at least used for indicating a current to-be-performed hospital visit operation of the user; and send the hospital visit instruction information to an information exchange server based on a user identifier of the user, so that the information exchange server sends the hospital visit instruction information to the user terminal, to complete the hospital visit operation;

the hospital visit information including at least one of a to-be-conducted hospital visit item, fee information about a to-be-conducted hospital visit item, a conducted hospital visit item, or result information about a conducted hospital visit item.

According to a ninth aspect of the embodiments of the present technology, a server is provided, including:

a processor; and a memory that is configured to store an instruction that can be executed by a processor;

the processor being configured to:

receive hospital visit instruction information, the hospital visit instruction information being at least used for indicating a current to-be-performed hospital visit operation of a user; and send the hospital visit instruction information to a user terminal based on a user identifier of the user.

According to a tenth aspect of the embodiments of the present technology, a user terminal is provided, including:

a processor; and a memory that is configured to store an instruction that can be executed by a processor;

the processor being configured to:

receive hospital visit instruction information, the hospital visit instruction information being at least used for indicating a current to-be-performed hospital visit operation of a user; and display the hospital visit instruction information on an information exchange interface that is between the user and a public social network identifier of a specified hospital.

BRIEF DESCRIPTION OF THE DRAWINGS

To describe the technical solutions of the embodiments of the present technology more clearly, the following briefly introduces the accompanying drawings required for describing the embodiments. Apparently, the accompanying drawings in the following description show only some embodiments of the present technology, and a person of ordinary skill in the art may still derive other drawings from these accompanying drawings without creative efforts.

FIG. 4 is a schematic diagram of a payment interface according to an embodiment of the present technology;

DESCRIPTION OF EMBODIMENTS

Figure 1:
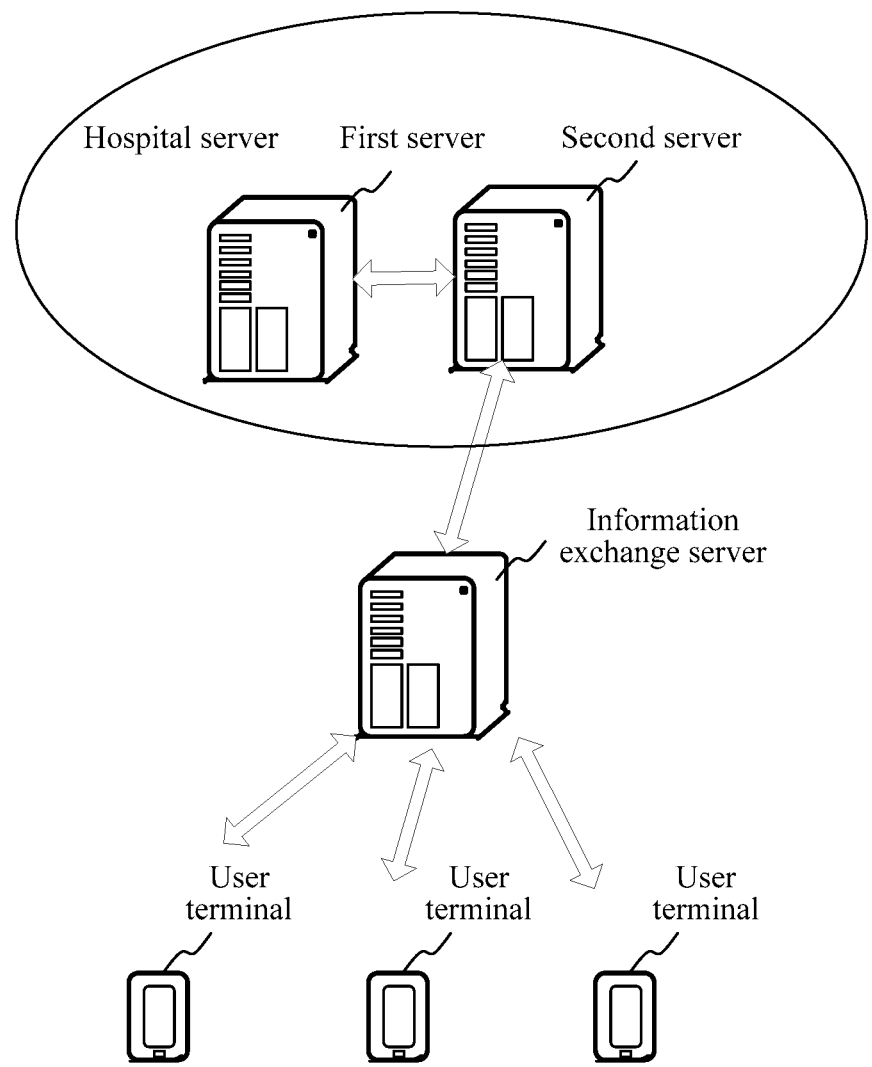
FIG. 1 is a schematic diagram of an information exchange system according to an embodiment of the present technology.

To make objectives, technical solutions, and advantages clearer, the following further describes implementation manners of the present technology in detail with reference to the accompanying drawings.

An information exchange platform refers to a network architecture that connects one person to another person by using social relationships and/or common interests (or common benefits). A user may perform daily communication and process some daily routines by using a client provided by the information exchange platform. Each user may have a network identity used for being identified by another user on the information exchange platform.

On the information exchange platform, different users may establish a social relationship in a manner of mutual confirmation, for example, adding each other as a friend or following each other. After two users establish a social relationship, they become social network contacts of each other on the social network platform provided by the information exchange platform. A group of users may form a mutual social relationship in a manner of voluntary selection, thereby forming a social group. Each member in the group is a social network contact of all other members in the group. The social network contacts can perform instant message exchanges, or exchanges of other content, such as images, voice recordings, video recordings, articles, web links, payments, etc. as messages in a conversation interface provided by a client-side application of the information exchange platform. Examples of social network platforms provided by the information exchange platform includes Facebook, Twitter, Whatsapp, Wechat, Yahoo Messenger, and the like.

A user or an organization may establish a public social network identifier on the information exchange platform, and allow the public (for example, any user on the information exchange platform) to communicate with the public social network identifier on the information exchange platform, where the communication may be based on a manner of one-way confirmation, without a need of mutual confirmation between users. For example, a user may choose to subscribe to (or follow) a public social network identifier (for example, "follow (follow)" a public account) message or release information, and become a social network contact of a public social network identifier in the manner of one-way confirmation such as subscription. An owner of a public social network identity may further use another user as a social network contact of the owner, where the another user is a user who has subscribed to a message of the owner or releases information.

Each user and each public social network identifier on the information exchange platform have a social network contact list, for the user and the public social network identifier to communicate with a user or a public social network identifier in the list in a form of an instant communication message. For example, users in a social group may communicate with each other by using an interface provided by the information exchange platform, and users may also communicate with each other by using an interface provided by the information exchange platform.

FIG. 1 is a schematic diagram of an information exchange system according to an embodiment of the present technology. As shown in the figure, the system includes a hospital server, an information exchange server, and at least one user terminal.

To ensure information security, the hospital server includes a first server and a second server. The first server may a hospital intranet server, and the second server may be a front-end server that connects a hospital intranet to an external network. A network firewall may be set between the first server and the second server, to ensure information security.

The first server is configured to generate hospital visit instruction information of a user according to hospital visit information of the user. The hospital visit instruction information is at least used for indicating a current to-be-performed hospital visit operation of the user. The hospital visit information includes at least one of a to-be-conducted hospital visit item, fee information about a to-be-conducted hospital visit item, a conducted hospital visit item, or result information about a conducted hospital visit item.

In this embodiment of the present technology, the first server is connected to multiple hospital terminals, and then the hospital visit instruction information of the user may be determined according to information sent by the hospital terminals. For example, when a doctor enters a to-be-conducted hospital visit item (e.g., an x-ray of the leg, a blood test order, a drug prescription, a follow-up consultation with a different specialist, etc.) of a user on a hospital terminal, the terminal sends information about the to-be-conducted hospital visit item to the first server, and the first server determines fee information of the to-be-conducted hospital visit item according to the to-be-conducted hospital visit item, and determines the to-be-conducted hospital visit item and the fee information of the to-be-conducted hospital visit item as hospital visit information of the user. In this embodiment of the present technology, the first server generates the hospital visit instruction information according to the hospital visit information of the user. For example, if the hospital visit information includes that a to-be-conducted hospital visit item is a routine blood test and fee information about the to-be-conducted hospital visit item is 70 RMB, generated hospital visit instruction information may be that "please pay 70 RMB, and perform the routine blood test in the F area on the second floor of the hospital". For another example, if the hospital visit information includes that a result of a conducted hospital visit item is a routine blood test report, generated hospital visit instruction information is "please view the blood routine report". It should be noted that, the hospital visit instruction information may further include other information such as a link address of to-be-viewed information, so that the user can click the hospital visit instruction information to obtain complete medical treatment information, for example, obtain a blood routine report. Specific content of the hospital visit instruction information is not limited in the present disclosure.

The second server is configured to send the hospital visit instruction information to an information exchange server, so that the information exchange server sends the hospital visit instruction information to the user terminal, to complete the hospital visit operation.

Specifically, the first server and the second server may interact with each other based on a hospital visit information number. However, when the second server and the information exchange server interact with each other, a user identifier used on the information exchange platform (e.g., the user's social network ID) needs to be used. Therefore, on the second server, a database of a hospital visit information number (e.g., a medical record number, or hospital registration number of the user) and a user identifier may be maintained, so that when receiving hospital visit information that carries any number, the first server determines a corresponding user identifier of the number according to the number. This user identifier may be an open ID or another user identifier used for interaction between platforms. Using only an open ID as an example, the open ID may be converted on the information exchange server into a user identifier that is on the information exchange platform, and the conversion may be performed based on a public social network identifier of the hospital server, or may be performed based on a conversion rule. This is not limited in this embodiment of the present technology. The second server sends hospital visit instruction information and a user identifier to the information exchange server, so that the information exchange server performs conversion according to the user identifier, and sends the hospital visit instruction information to a user according to a user identifier that is obtained after the conversion. When sending a request of a user and receiving information of a hospital server, the information exchange server has performed user identifier conversion, to protect patient privacy. Certainly, the open ID is only an account conversion form that provides security protection, and the information exchange server may further use another account conversion method, to perform effective identity isolation on the information exchange server and the first server.

The information exchange server is configured to: receive the hospital visit instruction information, where the hospital visit instruction information is at least used for indicating the current to-be-performed hospital visit operation of the user; and send the hospital visit instruction information to the user terminal.

The user terminal is configured to: receive the hospital visit instruction information, where the hospital visit instruction information is at least used for indicating the current to-be-performed hospital visit operation of the user; and display the hospital visit instruction information on an information exchange interface that is between the user and a public social network identifier of a hospital. Specifically, an information exchange application is installed on the user terminal, and a user may exchange information with a public social network identifier of a specified hospital based on the information exchange application.

By means of the information exchange system provided in this embodiment of the present technology, a hospital server generates hospital visit instruction information, and sends the hospital visit instruction information to an information exchange server based on a user identifier, and the information exchange server transmits the hospital visit instruction information to a user terminal based on the user identifier, so that the hospital visit instruction information is displayed on the user terminal. Therefore, efficiency of information exchange between a hospital and a user is increased, and a hospital visit process of the user is facilitated.

In an embodiment for a different application scenario, the information exchange system provided in this embodiment of the present technology may further have the following technical features.

In an embodiment of the present technology, the second server is further configured to receive registration request information of the user, where the registration request information includes at least the user identifier; and correspondingly, the first server is further configured to: receive the registration request information, and generate the hospital visit information of the user based on identity information carried in the registration request information, where the hospital visit information includes at least a to-be-conducted hospital visit item and fee information about a to-be-conducted hospital visit item; or generate the hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the first server is further configured to update the hospital visit information of the user according to an operation instruction of a hospital staffer. The hospital visit information includes at least one of a to-be-conducted hospital visit item, fee information about a to-be-conducted hospital visit item, a conducted hospital visit item, or result information about a conducted hospital visit item.

In an embodiment of the present technology, the second server is further configured to: establish a binding relationship between the hospital visit information of the user and the user identifier of the user, and invoke a hospital visit instruction information sending port according to the binding relationship, to send the hospital visit instruction information to the information exchange server in a form of a template message.

In an embodiment of the present technology, the first server is configured to: when the hospital visit information of the user includes fee information about a to-be-conducted hospital visit item, generate hospital visit instruction information according to the fee information about a to-be-conducted hospital visit item, where the hospital visit instruction information is at least used for indicating a current to-be-performed payment operation of the user; and correspondingly, when the second server receives payment completion confirmation information, the first server updates the hospital visit information of the user according to the payment completion confirmation information.

In an embodiment of the present technology, the information exchange server is configured to: receive a payment request of the user after sending the hospital visit instruction information to the user terminal, where the payment request includes payment verification information;

perform verification on the payment request of the user according to the payment verification information, and perform a money transfer operation according to the user identifier of the user and the public social network identifier of the hospital when the verification of the payment request of the user succeeds; and send payment completion confirmation information to the hospital server when the money transfer operation is completed, so that the hospital server updates the hospital visit information of the user according to the payment completion confirmation information.

In an embodiment of the present technology, the information exchange server is configured to establish a follow relationship between the user and the public social network identifier of the hospital.

In an embodiment of the present technology, the user terminal is further configured to: send registration request information to the information exchange server according to a trigger operation performed on a registration option by the user on the information exchange interface, where the registration request information includes at least the user identifier, and the registration request information is used for enabling the hospital server to receive the registration request information, and generate hospital visit information of the user based on identity information carried in the registration request information, where the hospital visit information includes at least a to-be-conducted hospital visit item and fee information about a to-be-conducted hospital visit item, or the registration request information is used for enabling the hospital server to generate hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the user terminal is further configured to: after displaying the hospital visit instruction information on the information exchange interface that is between the user and the public social network identifier of the hospital, monitor a clicking operation performed on the instruction information by the user on the information exchange interface; display a payment interface when detecting the clicking operation performed on the instruction information; and complete a payment process according to an operation performed by the user on the payment interface.

It should be noted that, in this embodiment of the present technology, division of servers is division in terms of functions, and does not relate to a specific device entity. That is, a server may be an independent physical device, or may be a functional apparatus on any physical device in a system. For example, the first server and the second server may be independent physical devices, or may be functional apparatuses in a physical device.

Figure 2:
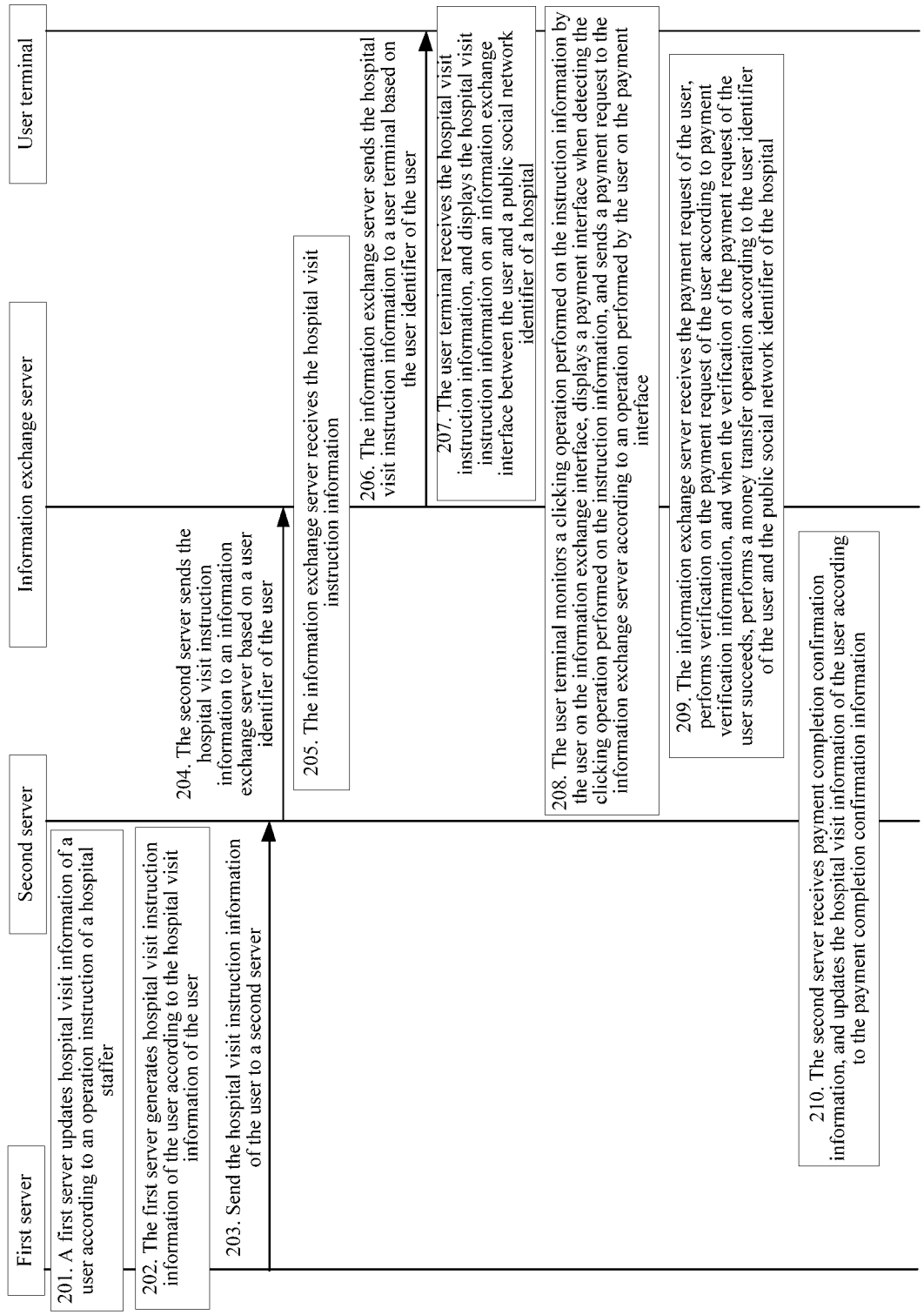
FIG. 2 is a flowchart of an information exchange method according to an embodiment of the present technology.

FIG. 2 is a flowchart of an information exchange method according to an embodiment of the present technology. The method is applied to the information exchange system, and the application scenario is payment during a hospital visit. As shown in FIG. 2, the method includes operation 201 to operation 210.

201: A first server updates hospital visit information of a user according to an operation instruction of a hospital staffer.

In this embodiment of the present technology, the hospital staffer enters the operation instruction on a hospital terminal according to an illness status of the user. For example, when a doctor considers after diagnosis that the user requires a routine blood test, the doctor enters an operation instruction of a to-be-conducted routine blood test of the user on the hospital terminal.

The hospital terminal sends the operation instruction to the first server, so that the first server updates the hospital visit information of the user. The hospital visit information includes at least a to-be-conducted hospital visit item and fee information about a to-be-conducted hospital visit item. The update includes adding an item, modifying an item, deleting an item, or the like. For example, after receiving the operation instruction of the to-be-conducted routine blood test of the user, the first server adds, to the hospital visit information of the user, fee information that 70 RMB is to be paid for the routine blood test.

202: The first server generates hospital visit instruction information of the user according to the hospital visit information of the user, where the hospital visit instruction information is at least used for indicating a current to-be-performed hospital visit operation of the user.

In this embodiment of the present technology, the hospital visit information of the user includes the fee information about a to-be-conducted hospital visit item, and then the hospital visit instruction information is generated according to the fee information about a to-be-conducted hospital visit item. The hospital visit instruction information is at least used for indicating the current to-be-performed treatment operation of the user, and the treatment operation includes a payment operation. For example, when the hospital visit information of the user includes fee information that the routine blood test is 70 RMB, hospital visit instruction information for indicating payment of 70 RMB is generated.

203: The first server sends the hospital visit instruction information of the user to a second server.

204: The second server sends the hospital visit instruction information to an information exchange server based on a user identifier of the user.

To send the hospital visit instruction information to a specified user, in this embodiment of the present technology, the second server establishes a binding relationship between the hospital visit information of the user and the user identifier of the user, and specifically binds the user identifier and a number of the hospital visit information. The number of the hospital visit information may be determined by the user during registration.

In this embodiment of the present technology, a process of interaction between the second server and the information exchange server may be based on a user identifier of an open ID type. The second server may determine, according to the binding relationship, an open ID corresponding to the hospital visit instruction information, and invoke a message sending interface to send the hospital visit instruction information to the information exchange server.

205: The information exchange server receives the hospital visit instruction information.

206: The information exchange server sends the hospital visit instruction information to a user terminal based on the user identifier of the user.

To accurately send the hospital visit instruction information to a specified user, in this embodiment of the present technology, the information exchange server provides a template message interface for the second server, and then the second server may send the hospital visit instruction information, so that the information exchange server receives the hospital visit instruction information.

In this embodiment of the present technology, after receiving the hospital visit instruction information, the information exchange server obtains, according to the open ID of the user, the user identifier that is of the user and that is on the information exchange server, and sends the hospital visit instruction information to the open ID of the user in a form of pushing a template message. The hospital visit instruction information is at least used for indicating a current to-be-performed hospital visit operation of the user. In this embodiment of the present technology, the hospital visit operation includes a payment operation.

207: The user terminal receives the hospital visit instruction information, and displays the hospital visit instruction information on an information exchange interface between the user and a public social network identifier of a hospital.

The hospital visit instruction information is at least used for indicating the current to-be-performed hospital visit operation of the patient. In this embodiment of the present technology, the hospital visit operation includes a payment operation.

An information exchange application is installed on the user terminal, and the user may follow the public social network identifier of the specified hospital based on the information exchange application, so that the information exchange server establishes a follow relationship between the user and the public social network identifier of the hospital. Based on the follow relationship, the user may exchange information with the public social network identifier of the specified hospital, and then receive the hospital visit instruction information.

Figure 3:
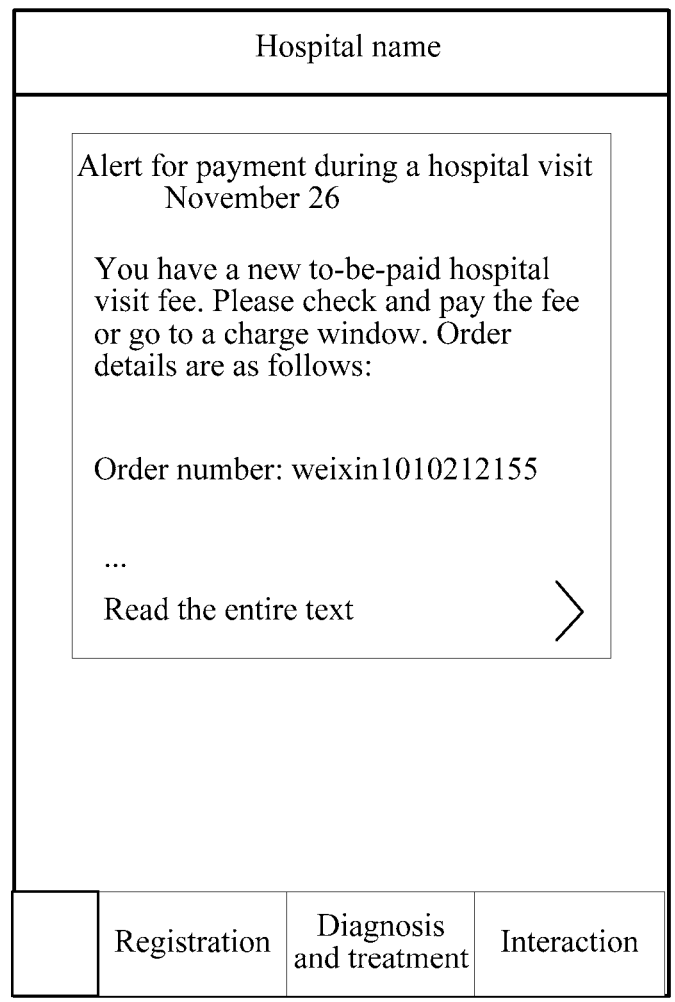
FIG. 3 is a schematic diagram of an information exchange interface according to an embodiment of the present technology.

The information exchange may be implemented based on an information exchange interface. As shown in FIG. 3, after the hospital visit instruction information is received, the information exchange interface displays the hospital visit instruction information. Specifically, the information exchange interface may include a message display area, and the hospital visit instruction information may be displayed in the message display area in a form of a message box, such as a payment alert message in FIG. 3.

208: The user terminal monitors a clicking operation performed on the indication information by the user on the information exchange interface, displays a payment interface when detecting the clicking operation performed on the indication information, and sends a payment request to the information exchange server according to an operation performed by the user on the payment interface.

The clicking operation performed on the indication operation refers to an operation of clicking, in the message display area of the information exchange interface, the message box that displays the hospital visit instruction information. As shown in FIG. 4, after the clicking, the payment interface is displayed on the original information exchange interface, and the payment interface may display fee information about a hospital visit item that needs to be paid for.

Further, completing a payment process according to the operation performed by the user on the payment interface includes: when the user clicks an option of payment confirmation, displaying a payment verification interface. The payment verification interface includes an area for entering payment verification information. Specifically, the payment verification information may be a payment password.

After completing entering the payment verification information, the user sends the payment request to the information exchange server. The payment request includes the payment verification information.

209: The information exchange server receives the payment request of the user, where the payment request includes payment verification information, performs verification on the payment request of the user according to the payment verification information, and performs a money transfer operation according to the user identifier of the user and the public social network identifier of the hospital when the verification of the payment request of the user succeeds.

After completing the money transfer operation, the information exchange server sends payment completion confirmation information to the second server.

It should be noted that, operation 209 is a specific implementation manner for completing payment. In the specific implementation manner, this embodiment of the present technology is described by using only an example in which fees are deducted, by means of interaction between the user terminal and the information exchange server, from an account bound to the user, thereby completing payment. In an actual application, the user may alternatively use another manner to complete payment. For example, the user completes payment based on a third-party payment platform, and then the third-party payment platform sends payment completion confirmation information to the information exchange server. Whether payment is completed by means of the interaction between the user terminal and the information exchange server is not specifically limited in the present disclosure.

210: The second server receives payment completion confirmation information, and updates the hospital visit information of the user according to the payment completion confirmation information.

The updating the hospital visit information of the user includes deleting the fee information about the to-be-conducted hospital visit item from the hospital visit information of the user, for example, after receiving completion information of payment of 70 RMB for the routine blood test, deleting fee information of 70 RMB for the to-be-conducted hospital visit item of the routine blood test from the hospital visit information.

After the hospital visit information of the user is updated, a next hospital visit operation may continue to be performed based on the updated hospital visit information. The next hospital visit operation is similar to operations 201 to 210 of the information exchange method.

By means of the information exchange method provided in this embodiment of the present technology, a hospital server generates hospital visit instruction information, and sends the hospital visit instruction information to an information exchange server based on a user identifier, and the information exchange server transmits the hospital visit instruction information to a user terminal based on the user identifier, so that the hospital visit instruction information is displayed on the user terminal. Therefore, a user may conveniently complete a hospital visit operation of payment during a hospital visit, increasing efficiency of information exchange between a hospital and the user, and facilitating a hospital visit process of the user.

Figure 5:
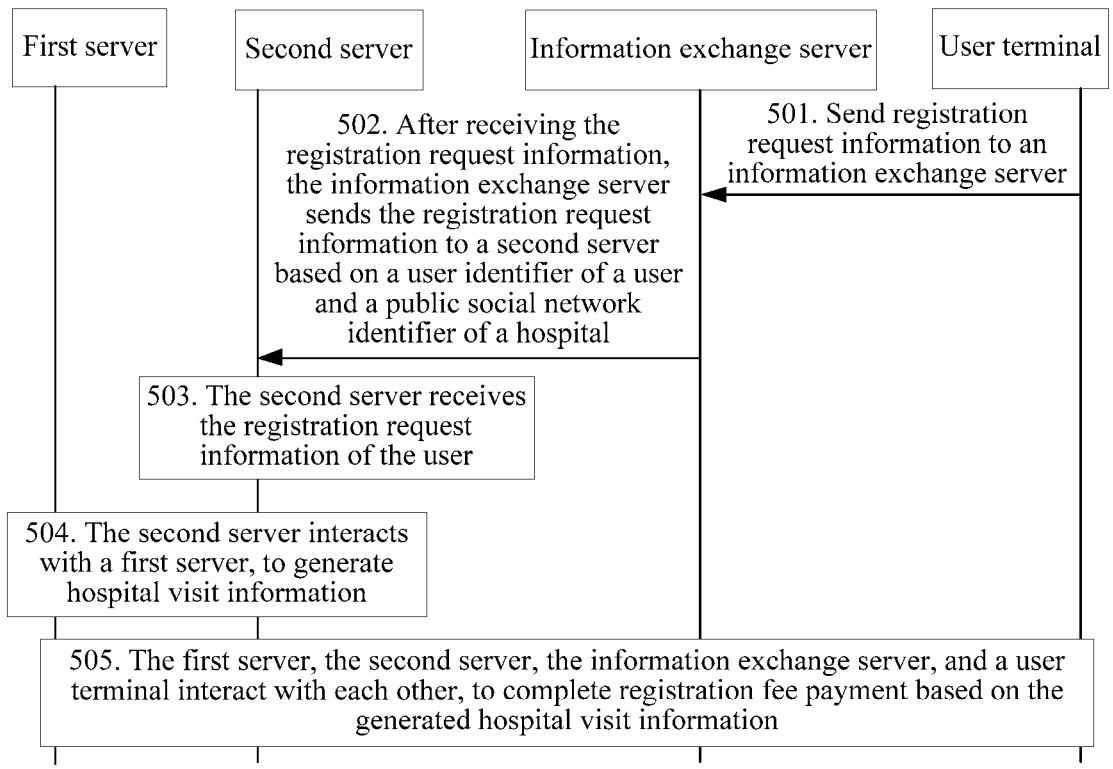
FIG. 5 is a flowchart of an information exchange method according to an embodiment of the present technology.

FIG. 5 is a flowchart of an information exchange method according to an embodiment of the present technology. The method is applied to the information exchange system, and the application scenario is registration. As shown in FIG. 5, the method includes operation 501 to operation 505.

501: A user terminal sends registration request information to an information exchange server according to a trigger operation performed on a registration option by a user on an information exchange interface.

The registration request information includes at least a user identifier. The registration request information may further include identity information, hospital visit time information, hospital visit department information, or the like of the user. The identity information includes the name, the age, medical history, or the like of the user.

An information exchange application is installed in the user terminal. An interaction interface of the information exchange application is shown in FIG. 3. Based on the information exchange application, the user may open the information exchange interface (e.g., a group chat interface) between the user and a public social network identifier of a hospital. A registration option is set on the information exchange interface, and the user may trigger the registration option by performing a click operation. In some embodiments, if the user is at the hospital, the user can select a check-in operation by scanning a barcode that is displayed at the hospital. In some embodiments, by scanning a barcode displayed at the hospital, the client terminal automatically opens a group chat including the user's social network identity and the public social network identity of the hospital, and the registration is started, and the user is given a registration number, and an instruction for paying a registration fee in the group chat interface. The user can choose to pay the registration fee using the payment account already set up with the information exchange server. Once the payment is made, the registration is completed and the user can exchange chat messages with the hospital for subsequent actions. For example, the user can enter one or more descriptions of a symptom, and the hospital server receives the description of the symptoms, and determines one or more appropriate departments that the user should be seen in, and automatically adds social network identities corresponding to those departments to the group chat. The user can choose to register with one or more of those departments, by clicking on the registration message sent from those departments. In some embodiments, a hospital personnel managing the public account of the hospital reads the description of the symptoms at a hospital terminal connected to the information exchange server, and determines which departments the user should visit, and sends the instruction information in chat messages to the user. In some embodiments, the user can type in the names of the department that he/she wishes to register for a visit in a chat message and send the message to the hospital staff via the group chat interface.

Preferably, after the registration option is triggered, an information filling interface is displayed, for filling various information that needs to be included in a registration request.

502: After receiving the registration request information, the information exchange server sends the registration request information to a second server based on a user identifier of the user and a public social network identifier of a hospital.

503: The second server receives the registration request information of the user.

The second server receives the registration request information by using a message interface provided by the information exchange server.

504: The second server interacts with a first server, to generate hospital visit information.

The first server interacts with the second server, to perform verification on the registration request information, for example, to perform verification on a hospital visit time and a hospital visit department in a registration request, to determine whether a hospital visit may be paid in the department at the time. When the verification succeeds, it is determined that registration may be performed, and then the hospital visit information is generated.

Specifically, in this embodiment of the present technology, different processing processes may be provided for registration for the first time and subsequent hospital visit registration.

For the registration for the first time, the first server generates hospital visit information of the user according to the registration request information based on identity information carried in the registration request information. The hospital visit information includes at least a to-be-conducted hospital visit item and fee information about a to-be-conducted hospital visit item. Specifically, the first server generates, according to the identity information in the registration request information, new hospital visit information for the user, and determines the to-be-conducted hospital visit item and the fee information about the to-be-conducted hospital visit item according to the hospital visit department information in the registration request. For example, when the hospital visit department information in the registration request is the stomatology department, it is determined that the to-be-conducted hospital visit item is a stomatology test, and the test fee is 10 RMB.

For subsequent registration, the first server generates hospital visit information of the user according to the user identifier based on identity information that is in history hospital visit information of the user. The hospital visit information includes at least a to-be-conducted hospital visit item and fee information about a to-be-conducted hospital visit item. Specifically, if the user has previously paid a hospital visit based on the user identifier, the first server may find, according to the user identifier, information required for registration from the history hospital visit information of the user, to generate the hospital visit information. For example, if the user has received stomatology test three days ago, that the to-be-conducted hospital visit item is the stomatology test and the test fee is 10 RMB is added based on the history hospital visit information, to generate new hospital visit information.

It should be noted that, hospital visit information of each user may have a number used for uniquely identifying the hospital visit information, so that on a side of the hospital server, information may be transmitted based on the number of the hospital visit information.

505: The first server, the second server, the information exchange server, and the user terminal interact with each other, to complete registration fee payment based on the generated hospital visit information.

Visit indication information is generated based on the generated hospital visit information. The hospital visit instruction information is used for indicating a registration fee payment operation that is to be performed by the user. A specific process is similar to operations 202 to 210, and details are not described herein again.

In this embodiment of the present technology, after the registration fee payment succeeds, information about a registration success is displayed on the user terminal. The information about the registration success includes information for reminding the user to perform a hospital visit at a specified location at a specified time.

By means of the information exchange method provided in this embodiment of the present technology, a user terminal sends registration request information, so that a hospital server generates hospital visit instruction information and sends the hospital visit instruction information to an information exchange server based on a user identifier, and the information exchange server transmits the hospital visit indication information to the user terminal based on the user identifier, so that the hospital visit indication information is displayed on the user terminal. Therefore, a user may conveniently complete a hospital visit operation of registration, increasing efficiency of information exchange between a hospital and the user, and facilitating a hospital visit process of the user.

Figure 6:
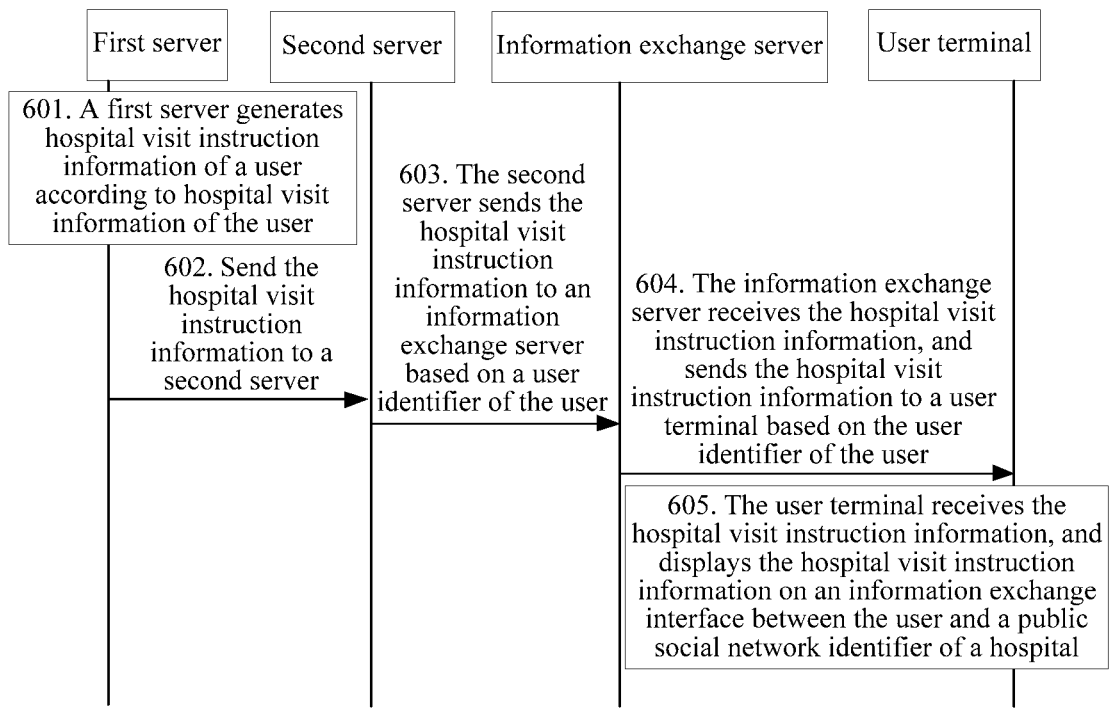
FIG. 6 is a flowchart of an information exchange method according to an embodiment of the present technology.

FIG. 6 is a flowchart of an information exchange method according to an embodiment of the present technology. The method is applied to the information exchange system, and the application scenario is viewing a hospital visit result. As shown in FIG. 6, the method includes operation 601 to operation 605.

601: A first server generates hospital visit instruction information of a user according to hospital visit information of the user.

In this embodiment, the hospital visit information includes at least a conducted hospital visit item and result information about a conducted hospital visit item. The result information about a conducted hospital visit item includes: doctor diagnosis information after a paid hospital visit, test report information after a conducted medical test, an imaging result after a conducted imaging test, or the like. In this embodiment, the hospital visit instruction information is at least used for indicating a current to-be-performed hospital visit operation of the user. The to-be-performed hospital visit operation includes an operation of viewing a hospital visit result. The hospital visit instruction information may further directly carry result information about a conducted hospital visit item.

It should be noted that, the conducted hospital visit item and the result information about a conducted hospital visit item may be entered by a hospital staffer on a hospital terminal, or may be automatically collected by a hospital terminal. For example, if the hospital visit item is seeing a doctor, a test result may be entered by the seen doctor on a hospital terminal, and if the hospital visit item is a medical test, a test result may be automatically collected by a hospital terminal. Sources of the conducted hospital visit item and the result information about a conducted hospital visit item are not limited in the present disclosure.

602: The first server sends the hospital visit instruction information to a second server.

603: The second server sends the hospital visit instruction information to an information exchange server based on a user identifier of the user.

Operation 603 is similar to operation 203, and details are not described herein again.

604: The information exchange server receives the hospital visit instruction information, and sends the hospital visit instruction information to a user terminal based on the user identifier of the user.

Operation 604 is similar to operation 204, and details are not described herein again.

605: The user terminal receives the hospital visit instruction information, and displays the hospital visit instruction information on an information exchange interface between the user and a public social network identifier of a hospital.

Subsequently, an operation on the user terminal is similar to operation 207, and details are not described herein again. A difference is only that the hospital visit instruction information is used for instructing the user to view the hospital visit result.

Preferably, after this operation, the user terminal monitors a clicking operation performed on the indication information by the user on the information exchange interface, and displays the result information about a conducted hospital visit item when detecting the clicking operation performed on the indication information.

It should be noted that, the information exchange method that is in a hospital visit process and that is provided in the foregoing embodiment may be applied to any scenario that requires a user and a hospital to interact with each other, but is not limited to the foregoing scenarios. However, there is no mutual absolute dependency between the foregoing scenarios, and a scenario such as payment during a hospital visit or querying for a diagnosis and treatment result may be implemented as long as in any scenario process, a user follows a public social network identifier of the hospital and performs a corresponding hospital visit operation based on the follow relationship.

By means of the information exchange method provided in this embodiment of the present technology, a hospital server generates hospital visit instruction information, and sends the hospital visit instruction information to an information exchange server based on a user identifier, and the information exchange server transmits the hospital visit instruction information to a user terminal based on the user identifier, so that the hospital visit instruction information is displayed on the user terminal. Therefore, a user may conveniently complete a hospital visit operation of viewing a hospital visit result, increasing efficiency of information exchange between a hospital and the user, and facilitating a hospital visit process of the user.

Based on the above, in some embodiments, A method of supporting hospital visits on a social network platform, comprising: at a client terminal having one or more processors and memory: detecting a user input for registering a visit at a hospital using a social network client application of the social network platform; in response to detecting the user input: obtaining a registration number for the visit, wherein the registration number indicates an ordinal position of the user in a hospital queue of multiple visitors to the hospital; displaying a group chat interface for a group conversation including a social network identity of the user and a public social network identity of the hospital; and displaying a payment request for the visit in the group chat interface. In some embodiments, the user can pay for the visit (e.g., registration fee) by using a payment account already associated with the social network identity of the user on the social network platform. In some embodiments, the user can forward the payment request to another user on the social network platform, and let that other user pay for the registration fee. In some embodiments, the user can add one or more other users to the group conversation, such that the other users can choose to pay for the registration fee on their respective client terminals using their respective payment accounts associated with the social network platform. In some embodiments, if the paying user is not added to the group conversation, a payment receipt is generated in response to the payment, and the paying user can forward the payment receipt to the user visiting the hospital. Once the payment is made, the hospital server can set up the medical record and start the subsequent hospital visit procedures.

In some embodiments, displaying the group chat interface for the group conversation including the social network identity of the user and the public social network identity of the hospital includes: in response to detecting the user input: determining whether the group conversation between the social network identity of the user and the public social network identity of the hospital already exists on the client terminal; in accordance with a determination that the group conversation between the social network identity of the user and the public social network identity of the hospital does not already exists on the client terminal: sending a request to a server of the social network platform to establish the group conversation; and displaying the group chat interface for the group conversation; and in accordance with a determination that the group conversation between the social network identity of the user and the public social network identity of the hospital already exists on the client terminal: bringing the group chat interface for the group conversation to a foreground of the social network client application. For example, if a group conversation with the hospital already existed on the client terminal of the user, the group conversation is brought up to the foreground of the social network application running on the client terminal, and the user can see the previous message exchanges between the user and the hospital and call up past medical records. Similarly, the hospital staff can also call up the medical record from the group conversation log. In some embodiments, previously visited department is alerted, if a new department is visited. In some embodiments, if a new prescription is entered by the new department, the previously visited departments that have given prescriptions to the user are alerted, so that the doctors from those departments can review the new prescription and make sure no conflict would arise from the new prescription. In some embodiments, the doctors from the different department can exchange information and opinions in the group conversation, so that the user is aware of the discussions concerning his/her illness.

In some embodiments, detecting the user input for registering the visit at the hospital using the social network client application of the social network platform includes scanning a barcode associated with the hospital. For example, when the user arrives at the hospital, the user uses the social network client application to scan a barcode posted at the registration counter, and obtains a registration number and registration payment request. In some embodiments, the user also scans different barcodes when arriving at check-in counter of different departments that he/she supposed to visit. For example, for various departments that require a wait (e.g., labs, pharmacy, etc.), different registration numbers are obtained to indicate the ordinal positions of the user in the various queues at those departments. In some embodiments, the user may be placed in different queues, and the server of the social network platform or the hospital server can suggest a route for the user to visit the different departments based on the wait time and locations of the different departments.

In some embodiments, the client terminal receives an alert message from the public social network identity of the hospital, the alert message indicating an estimated wait time for checking-in for the visit; in response to receiving the alert message, the client terminal displays the alert message in the group chat interface of the group conversation between the social network identity of the user and the public social network identity of the hospital. For example, if the user's appointment time, and position in a lab queue is coming up for check in within 5 min based on estimated wait time, the hospital server sends an alert to the user via the social network platform, so the user can get ready to arrive on time.

In some embodiments, the client terminal receives description of one or more symptoms from the user in the group chat interface; the terminal sends the description of the one or more symptoms to the public social network identity of the hospital; the terminal then receives instruction from a hospital server to add social network identities of one or more hospital departments to the group conversation; and in response to receiving the instruction from the hospital server, the client terminal adds the social network identities of the one or more hospital departments to the group conversation. For example, if the user describes her symptoms with "headaches, fever, blurred vision, and nausea" in a message in the group conversation, the message is reviewed by a hospital staff, and determines that the user should be seen by an internal medicine doctor, the hospital staff requests the social network server to add an assigned internal medicine doctor to the group conversation based on the availability of the internal medicine doctors at the hospital. If the staff determines that the user should be seen by a specialist, the specialist is also added to the group conversation. The internal medicine doctor and the specialist will both receive notification that they are now in a group conversation with the user. In some embodiments, additional registration and payment requests are generated by the hospital server and displayed in the group conversation interface at the client terminal.

In some embodiments, the client terminal displays social network identities of a plurality of hospital departments associated with the hospital in the group chat interface. For example, a menu of departments are displayed in the group chat interface that are selectable by the user. The client terminal receives user input selecting one or more of the plurality of hospital departments in the group chat interface; and in response to receiving the user input selecting the one or more of the plurality of hospital departments in the group chat interface: the client terminal obtains respective registration numbers for each of the one or more hospital departments; and adds social network identities of the one or more hospital departments to the group conversation.

In some embodiments, the client terminal receives a user input adding one or more additional users to the group conversation; and in response to receiving the input adding the one or more additional users to the group conversation, the client terminal adds social network identities of the one or more additional users to the group conversation, wherein the payment request is visible to each of the one or more additional users in a corresponding group chat interface displayed on a respective client terminal of the additional user, and wherein the payment request is payable by the additional user using a payment account of the additional user.

Other details of the method, and operations of the corresponding hospital server and social network server correspond to the operations of the client terminal, and are apparent to a person of ordinary skills in the art in light of the disclosure provided herein, and are not repeated in the interest of brevity. Different features disclosed herein may be combined in various embodiments without limitation, unless specifically stated.

Figure 7:
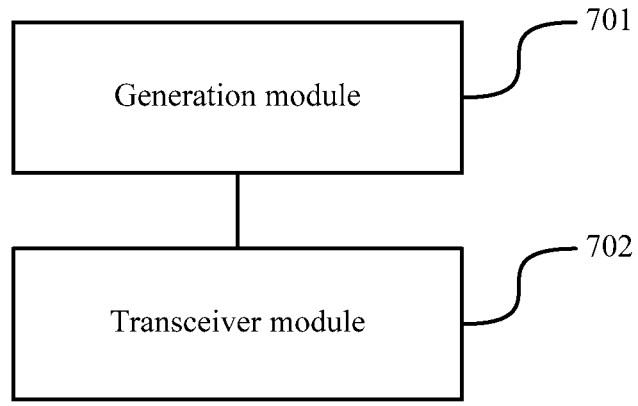
FIG. 7 is a block diagram of an information exchange apparatus according to an embodiment of the present technology.

FIG. 7 is a block diagram of an information exchange apparatus according to an embodiment of the present technology. As shown in FIG. 7, the apparatus includes a generation module 701 and a transceiver module 702.

The generation module 701 is configured to generate hospital visit instruction information of a user according to hospital visit information of the user. The hospital visit instruction information is at least used for indicating a current to-be-performed hospital visit operation of the user.

The transceiver module 702 is configured to send the hospital visit instruction information to an information exchange server based on a user identifier of the user, so that the information exchange server sends the hospital visit instruction information to the user terminal, to complete the hospital visit operation.

The hospital visit information includes at least one of a to-be-conducted hospital visit item, fee information about a to-be-conducted hospital visit item, a conducted hospital visit item, or result information about a conducted hospital visit item.

In an embodiment of the present technology, registration request information of the user is received, where the registration request information includes at least the user identifier. Correspondingly, the generation module is further configured to: generate the hospital visit information of the user according to the registration request information based on identity information carried in the registration request information, where the hospital visit information includes at least a to-be-conducted hospital visit item and fee information about a to-be-conducted hospital visit item; or generate the hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the generation module is further configured to update hospital visit information of the user according to an operation instruction of a hospital staffer. The hospital visit information includes at least one of a to-be-conducted hospital visit item, fee information about a to-be-conducted hospital visit item, a conducted hospital visit item, or result information about a conducted hospital visit item.

In an embodiment of the present technology, the transceiver module is further configured to: establish a binding relationship between the hospital visit information of the user and the user identifier of the user, and invoke a hospital visit instruction information sending port according to the binding relationship, to send the hospital visit instruction information to the information exchange server in a form of a template message.

In an embodiment of the present technology, the generation module is configured to: when the hospital visit information of the user includes fee information about a to-be-conducted hospital visit item, generate hospital visit instruction information according to the fee information about a to-be-conducted hospital visit item, where the hospital visit instruction information is at least used for indicating a current to-be-performed payment operation of the user. Correspondingly, when the transceiver module receives payment completion confirmation information, the generation module is further configured to update the hospital visit information of the user according to the payment completion confirmation information.

Figure 8:
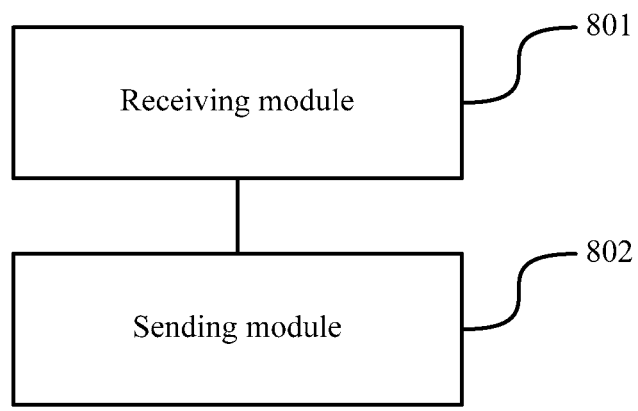
FIG. 8 is a block diagram of an information exchange apparatus according to an embodiment of the present technology.

FIG. 8 is a block diagram of an information exchange apparatus according to an embodiment of the present technology. As shown in FIG. 8, the apparatus includes a receiving module 801 and a sending module 802.

The receiving module 801 is configured to receive hospital visit instruction information. The hospital visit instruction information is at least used for indicating a current to-be-performed hospital visit operation of a user.

The sending module 802 is configured to send the hospital visit instruction information to a user terminal based on a user identifier of the user.

In an embodiment of the present technology, the apparatus further includes: a payment request receiving module, configured to receive a payment request of the user, where the payment request includes payment verification information; a verification module, configured to perform verification on the payment request of the user according to the payment verification information, and when the verification of the payment request of the user succeeds, perform a money transfer operation according to the user identifier of the user and the public social network identifier of the hospital; and a confirmation information sending module, configured to send payment completion confirmation information to the hospital server when the money transfer operation is completed, so that the hospital server updates the hospital visit information of the user according to the payment completion confirmation information.

In an embodiment of the present technology, the apparatus further includes: a follow module, configured to establish a follow relationship between the user and the public social network identifier of the hospital.

Figure 9:
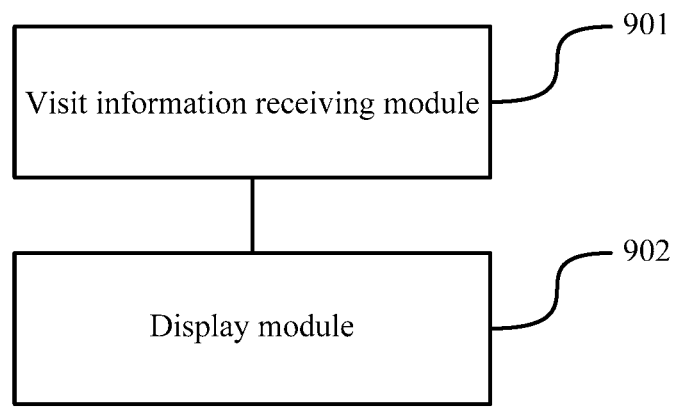
FIG. 9 is a block diagram of an information exchange apparatus according to an embodiment of the present technology.

FIG. 9 is a block diagram of an information exchange apparatus according to an embodiment of the present technology. As shown in FIG. 9, the apparatus includes a hospital visit information receiving module 901 and a display module 902.

The hospital visit information receiving module 901 is configured to receive hospital visit instruction information, the hospital visit instruction information being at least used for indicating a current to-be-performed hospital visit operation of a patient.

The display module 902 is configured to display the hospital visit instruction information on an information exchange interface that is between the user and a public social network identifier of a hospital.

In an embodiment of the present technology, the apparatus further includes: a registration module, configured to: send registration request information to the information exchange server according to a trigger operation performed on a registration option by the user on the information exchange interface, where the registration request information includes at least the user identifier, and the registration request information is used for enabling the hospital server to generate the hospital visit information of the user according to the registration request information based on identity information carried in the registration request information, where the hospital visit information includes at least a to-be-conducted hospital visit item and fee information about a to-be-conducted hospital visit item, or the registration request information is used for enabling the hospital server to generate hospital visit information of the user according to the user identifier based on identity information that is in history hospital visit information of the user, where the hospital visit information includes at least a to-be-conducted hospital visit item and fee information about a to-be-conducted hospital visit item.

In an embodiment of the present technology, the apparatus further includes: a detection module, configured to monitor a clicking operation performed on the hospital visit instruction information by the user on the information exchange interface; a payment display module, configured to display a payment interface when detecting the clicking operation performed on the hospital visit instruction information; and a payment operation module, configured to complete a payment process according to an operation performed by the user on the payment interface.

Figure 10:
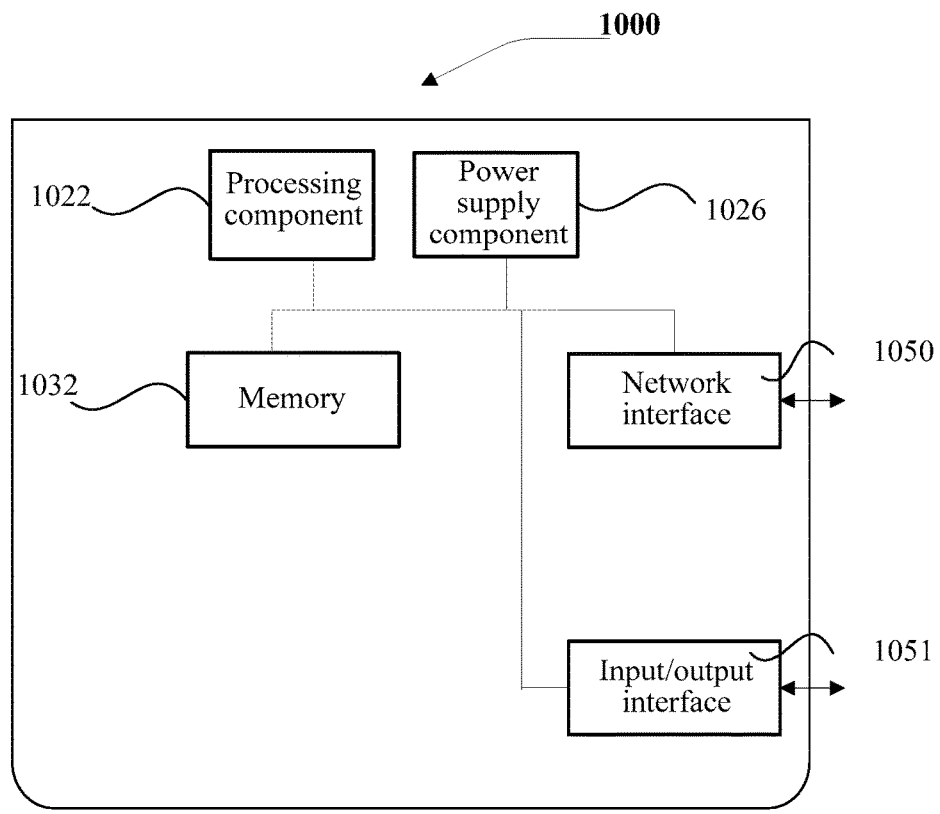
FIG. 10 is a block diagram of a server 1000 according to an embodiment of the present technology.

FIG. 10 is a block diagram of an information exchange server 1000 according to an embodiment of the present technology. The information exchange server may be configured as the first server or the second server in the foregoing hospital server, or may be configured as the information exchange server. Referring to FIG. 10, the server 1000 includes a processing component 1022, and the server 1000 further includes one or more processors, and a memory resource represented by a memory 1032. The memory resource is used for storing an instruction that can be executed by the processing component 1022, for example, an application program. An application program stored in the memory 1032 may include one or more modules, where each module corresponds to one set of instructions. In addition, the processing component 1022 is configured as an executable instruction, to execute the information exchange method in FIG. 2, FIG. 5, or FIG. 6.

The server 1000 may further include a power supply component 1026, configured to perform power supply management of the server 1000, a wired or wireless network interface 1050, configured to connect the server 1000 to a network, and an input/output (I/O) interface 1051. The server 1000 may operate an operating system that is stored in the memory 1032, for example, Windows Server™, Mac OS X™, Unix™, Linux™, or FreeBSD™.

Figure 11:
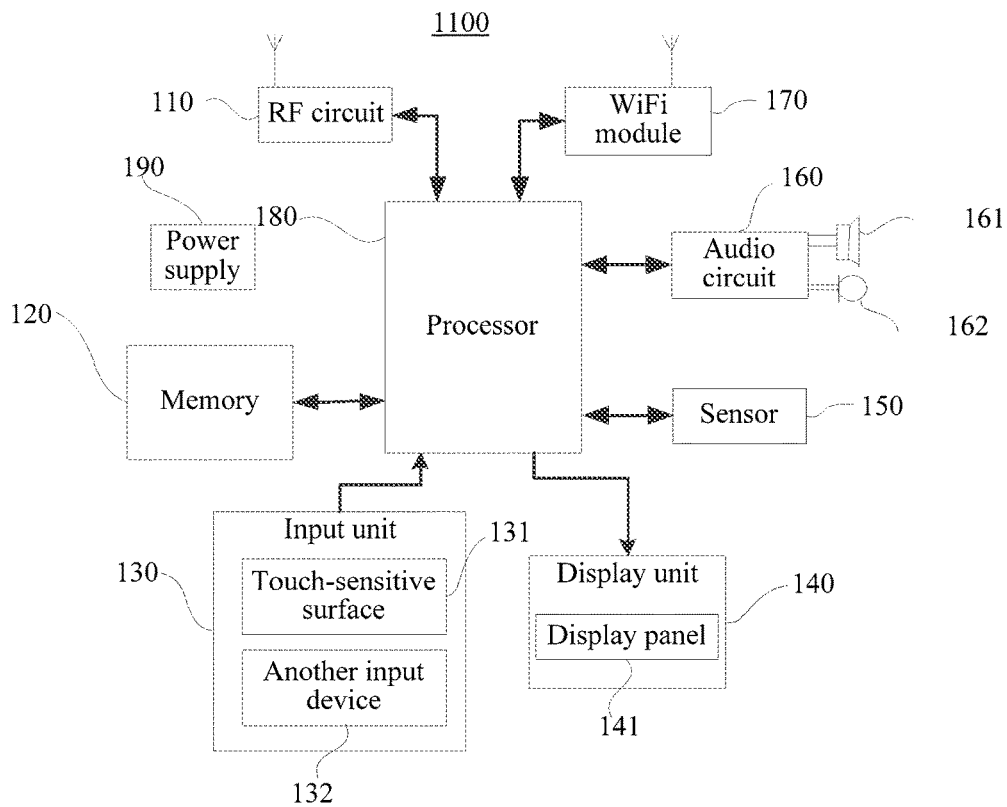
FIG. 11 is a block diagram of a user terminal 1100 according to an embodiment of the present technology.

FIG. 11 is a block diagram of an information exchange user terminal 1100 according to an embodiment of the present technology. Referring to FIG. 11, the terminal 1100 includes:

components such as a radio frequency (RF) circuit 110, a memory 120 including one or more computer readable storage media, an input unit 130, a display unit 140, a sensor 150, an audio circuit 160, a wireless fidelity (WiFi) module 170, a processor 180 including one or more processing cores, and a power supply 190. A person skilled in the art may understand that the structure of the terminal shown in FIG. 11 does not constitute a limitation to the terminal, and the terminal may include more components or fewer components than those shown in the figure, or some components may be combined, or a different component deployment may be used.

The RF circuit 110 may be configured to receive and send signals during an information receiving and sending process or a call process. Particularly, the RF circuit receives downlink information from a base station, then delivers the downlink information to one or more processors 180 for processing, and sends related uplink data to the base station. Generally, the RF circuit 110 includes, but is not limited to, an antenna, at least one amplifier, a tuner, one or more oscillators, a subscriber identity module (SIM) card, a transceiver, a coupler, a low noise amplifier (LNA), and a duplexer. In addition, the RF circuit 110 may also communicate with a network and another device by wireless communication. The wireless communication may use any communications standard or protocol, which includes, but is not limited to, Global System for Mobile communications (GSM), General Packet Radio Service (GPRS), Code Division Multiple Access (CDMA), Wideband Code Division Multiple Access (WCDMA), Long Term Evolution (LTE), email, Short Messaging Service (SMS), and the like.

The memory 120 may be configured to store a software program and module. The processor 180 runs the software program and module stored in the memory 120, to implement various functional applications and data processing. The memory 120 may mainly include a program storage area and a data storage area. The program storage area may store an operating system, an application program required by at least one function (such as a sound playback function and an image display function), and the like. The data storage area may store data (such as audio data and an address book) created according to use of the terminal 1100, and the like. In addition, the memory 120 may include a high speed random access memory, and may also include a non-volatile memory, such as at least one magnetic disk storage device, a flash memory, or another volatile solid-state storage device. Correspondingly, the memory 120 may further include a memory controller, so as to provide access of the processor 180 and the input unit 130 to the memory 120.

The input unit 130 may be configured to receive input digit or character information, and generate a keyboard, mouse, joystick, optical, or track ball signal input related to the user setting and function control. Specifically, the input unit 130 may include a touch-sensitive surface 131 and another input device 132. The touch-sensitive surface 131, which may also be referred to as a touchscreen or a touch panel, may collect a touch operation of a user on or near the touch-sensitive surface 131 (such as an operation of a user on or near the touch-sensitive surface 131 by using any suitable object or accessory, such as a finger or a stylus), and drive a corresponding connection apparatus according to a preset program. Optionally, the touch-sensitive surface 131 may include two parts: a touch detection apparatus and a touch controller. The touch detection apparatus detects a touch position of the user, detects a signal generated by the touch operation, and transfers the signal to the touch controller. The touch controller receives the touch information from the touch detection apparatus, converts the touch information into touch point coordinates, and sends the touch point coordinates to the processor 180. Moreover, the touch controller can receive and execute a command sent from the processor 180. In addition, the touch-sensitive surface 131 may be a resistive, capacitive, infrared, or surface sound wave type touch-sensitive surface. In addition to the touch-sensitive surface 131, the input unit 130 may further include the another input device 132. Specifically, the another input device 132 may include, but is not limited to, one or more of a physical keyboard, a functional key (such as a volume control key or a switch key), a track ball, a mouse, and a joystick.

The display unit 140 may be configured to display information input by the user or information provided for the user, and various graphical user interfaces of the terminal 1100. The graphical user interfaces may include graphs, texts, icons, videos, or any combination thereof. The display unit 140 may include a display panel 141. Optionally, the display panel 141 may be configured by using a liquid crystal display (LCD), an organic light-emitting diode (OLED), or the like. Further, the touch panel 131 may cover the display panel 141. After detecting a touch operation on or near the touch-sensitive surface 131, the touch-sensitive surface 131 transfers the touch operation to the processor 180, so as to determine the type of the touch event. Then, the processor 180 provides a corresponding visual output on the display panel 141 according to the type of the touch event. Although, in FIG. 11, the touch-sensitive surface 131 and the display panel 141 are used as two separate parts to implement input and output functions, in some embodiments, the touch-sensitive surface 131 and the display panel 141 may be integrated to implement the input and output functions.

The terminal 1100 may further include at least one sensor 150, such as an optical sensor, a motion sensor, and other sensors. Specifically, the optical sensor may include an ambient light sensor and a proximity sensor. The ambient light sensor may adjust luminance of the display panel 141 according to brightness of the ambient light. The proximity sensor may switch off the display panel 141 and/or backlight when the terminal 1100 is moved to the ear. As one type of motion sensor, a gravity acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, and an infrared sensor, which may be configured in the terminal 1100, are not further described herein.

The audio circuit 160, a loudspeaker 161, and a microphone 162 may provide audio interfaces between the user and the terminal 1100. The audio circuit 160 may convert received audio data into an electric signal and transmit the electric signal to the loudspeaker 161. The loudspeaker 161 converts the electric signal into a sound signal for output. On the other hand, the microphone 162 converts a collected sound signal into an electric signal. The audio circuit 160 receives the electric signal and converts the electric signal into audio data, and outputs the audio data to the processor 180 for processing. Then, the processor 180 sends the audio data to, for example, another terminal by using the RF circuit 110, or outputs the audio data to the memory 120 for further processing. The audio circuit 160 may further include an earplug jack, so as to provide communication between a peripheral earphone and the terminal 1100.

The WiFi is based on a short distance wireless transmission technology. The terminal 1100 may help, by using the WiFi module 170, the user to receive and send e-mails, browse a web page, access streaming media, and so on, which provides wireless broadband Internet access for the user. Although FIG. 11 shows the WiFi module 170, it may be understood that the WiFi module 170 is not a necessary component of the terminal 1100, and when required, the WiFi module 170 may be omitted as long as the scope of the essence of the present disclosure is not changed.

The processor 180 is a control center of the terminal 1100, is connected to various parts of the entire mobile phone by using various interfaces and lines, and by running or executing a software program and/or module stored in the memory 120 and invoking data stored in the memory 120, performs various functions of the terminal 1100 and process data, so as to perform overall monitoring on the mobile phone. Optionally, the processor 180 may include one or more processing cores. Preferably, the processor 180 may integrate an application processor and a modem processor. The application processor mainly processes an operating system, a user interface, an application program, and the like. The modem processor mainly processes wireless communication. It may be understood that the foregoing modem processor may alternatively not be integrated into the processor 180.

The terminal 1100 further includes the power supply 190 (such as a battery) for supplying power to the components. Preferably, the power supply may be logically connected to the processor 180 by using a power management system, thereby implementing functions such as charging, discharging, and power consumption management by using the power management system. The power supply 190 may further include one or more direct current or alternating current power supplies, a re-charging system, a power failure detection circuit, a power supply converter or inverter, a power supply state indicator, and any other components.

Although not shown in the figure, the terminal 1100 may further include a camera, a Bluetooth module, and the like, which are not further described herein. Specifically, in this embodiment, the display unit of the terminal is a touchscreen display. The terminal further includes a memory and one or more programs. The one or more programs are stored in the memory and configured to be executed by one or more processors. The one or more programs include instructions used for performing the following operations: receiving hospital visit instruction information, the hospital visit instruction information being at least used for indicating a current to-be-performed hospital visit operation of a patient; and displaying the hospital visit instruction information on an information exchange interface that is between the user and a public social network identifier of a specified hospital.

The one or more programs further include an instruction that is used for performing another operation in the information exchange method in FIG. 2, FIG. 6, or FIG. 7.

A person of ordinary skill in the art may understand that all or some of the operations of the foregoing embodiments may be implemented by using hardware, or may be implemented by a program instructing relevant hardware. The program may be stored in a computer readable storage medium. The storage medium may be a read-only memory, a magnetic disk, an optical disc, or the like.

The foregoing descriptions are merely preferred embodiments of the present technology, but are not intended to limit the present disclosure. Any modification, equivalent replacement, or improvement made within the spirit and principle of the present disclosure shall fall within the protection scope of the present disclosure.

What is claimed is:

1. A method of supporting hospital visits on a social network platform, comprising:
at a client terminal having one or more processors and memory:
detecting a user input for registering a visit at a hospital using a social network client application of the social network platform by scanning a barcode associated with the hospital;
in response to detecting the user input:
obtaining a registration number for the visit, wherein the registration number indicates an ordinal position of the user in a hospital queue of multiple visitors to the hospital;
displaying a group chat interface for a group conversation including a social network identity of the user and a public social network identity of the hospital; and
displaying a payment request for the visit in the group chat interface.

2. The method of claim 1, wherein displaying the group chat interface for the group conversation including the social network identity of the user and the public social network identity of the hospital includes:
in response to detecting the user input:
determining whether the group conversation between the social network identity of the user and the public social network identity of the hospital already exists on the client terminal;
in accordance with a determination that the group conversation between the social network identity of the user and the public social network identity of the hospital does not already exist on the client terminal:
sending a request to a server of the social network platform to establish the group conversation; and
displaying the group chat interface for the group conversation; and
in accordance with a determination that the group conversation between the social network identity of the user and the public social network identity of the hospital already exists on the client terminal:
bringing the group chat interface for the group conversation to a foreground of the social network client application.

3. The method of claim 1, including:
receiving an alert message from the public social network identity of the hospital, the alert message indicating an estimated wait time for checking-in for the visit;
in response to receiving the alert message, displaying the alert message in the group chat interface of the group conversation between the social network identity of the user and the public social network identity of the hospital.

4. The method of claim 1, including:
receiving description of one or more symptoms from the user in the group chat interface;
sending the description of the one or more symptoms to the public social network identity of the hospital;
receiving instruction from a hospital server to add social network identities of one or more hospital departments to the group conversation; and
in response to receiving the instruction from the hospital server, adding the social network identities of the one or more hospital departments to the group conversation.

5. The method of claim 1, including:
displaying social network identities of a plurality of hospital departments associated with the hospital in the group chat interface;
receiving user input selecting one or more of the plurality of hospital departments in the group chat interface; and
in response to receiving the user input selecting the one or more of the plurality of hospital departments in the group chat interface:
obtaining respective registration numbers for each of the one or more hospital departments; and
adding social network identities of the one or more hospital departments to the group conversation.

6. The method of claim 1, including:
receiving a user input adding one or more additional users to the group conversation;
in response to receiving the input adding the one or more additional users to the group conversation, adding social network identities of the one or more additional users to the group conversation, wherein the payment request is visible to each of the one or more additional users in a corresponding group chat interface displayed on a respective client terminal of the additional user, and wherein the payment request is payable by the additional user using a payment account of the additional user.

7. A client device for supporting hospital visits on a social network platform, comprising:
one or more processors; and
memory storing instructions, the instructions, when executed by the one or more processors, cause the processors to perform operations comprising:
detecting a user input for registering a visit at a hospital using a social network client application of the social network platform by scanning a barcode associated with the hospital;
in response to detecting the user input:
obtaining a registration number for the visit, wherein the registration number indicates an ordinal position of the user in a hospital queue of multiple visitors to the hospital;
displaying a group chat interface for a group conversation including a social network identity of the user and a public social network identity of the hospital; and
displaying a payment request for the visit in the group chat interface.

8. The client device of claim 7, wherein displaying the group chat interface for the group conversation including the social network identity of the user and the public social network identity of the hospital includes:
in response to detecting the user input:
determining whether the group conversation between the social network identity of the user and the public social network identity of the hospital already exists on the client terminal;
in accordance with a determination that the group conversation between the social network identity of the user and the public social network identity of the hospital does not already exist on the client terminal:
sending a request to a server of the social network platform to establish the group conversation; and
displaying the group chat interface for the group conversation; and
in accordance with a determination that the group conversation between the social network identity of the user and the public social network identity of the hospital already exists on the client terminal:
bringing the group chat interface for the group conversation to a foreground of the social network client application.

9. The client device of claim 7, wherein the operations further include:
receiving an alert message from the public social network identity of the hospital, the alert message indicating an estimated wait time for checking-in for the visit;
in response to receiving the alert message, displaying the alert message in the group chat interface of the group conversation between the social network identity of the user and the public social network identity of the hospital.

10. The client device of claim 7, wherein the operations further include:
receiving description of one or more symptoms from the user in the group chat interface;
sending the description of the one or more symptoms to the public social network identity of the hospital;
receiving instruction from a hospital server to add social network identities of one or more hospital departments to the group conversation; and
in response to receiving the instruction from the hospital server, adding the social network identities of the one or more hospital departments to the group conversation.

11. The client device of claim 7, wherein the operations further include:
displaying social network identities of a plurality of hospital departments associated with the hospital in the group chat interface;
receiving user input selecting one or more of the plurality of hospital departments in the group chat interface; and
in response to receiving the user input selecting the one or more of the plurality of hospital departments in the group chat interface:
obtaining respective registration numbers for each of the one or more hospital departments; and
adding social network identities of the one or more hospital departments to the group conversation.

12. The client device of claim 7, wherein the operations further include:
receiving a user input adding one or more additional users to the group conversation;
in response to receiving the input adding the one or more additional users to the group conversation, adding social network identities of the one or more additional users to the group conversation, wherein the payment request is visible to each of the one or more additional users in a corresponding group chat interface displayed on a respective client terminal of the additional user, and wherein the payment request is payable by the additional user using a payment account of the additional user.

13. A non-transitory computer-readable storage medium for supporting hospital visits on a social network platform, the computer-readable storage medium storing instructions, which, when executed by one or more processors of a client terminal, cause the client terminal to perform operations comprising:
detecting a user input for registering a visit at a hospital using a social network client application of the social network platform by scanning a barcode associated with the hospital;
in response to detecting the user input:
obtaining a registration number for the visit, wherein the registration number indicates an ordinal position of the user in a hospital queue of multiple visitors to the hospital;
displaying a group chat interface for a group conversation including a social network identity of the user and a public social network identity of the hospital; and
displaying a payment request for the visit in the group chat interface.

14. The computer-readable storage medium of claim 13, wherein displaying the group chat interface for the group conversation including the social network identity of the user and the public social network identity of the hospital includes:
in response to detecting the user input:
determining whether the group conversation between the social network identity of the user and the public social network identity of the hospital already exists on the client terminal;
in accordance with a determination that the group conversation between the social network identity of the user and the public social network identity of the hospital does not already exist on the client terminal:
sending a request to a server of the social network platform to establish the group conversation; and
displaying the group chat interface for the group conversation; and
in accordance with a determination that the group conversation between the social network identity of the user and the public social network identity of the hospital already exists on the client terminal:
bringing the group chat interface for the group conversation to a foreground of the social network client application.

15. The computer-readable storage medium of claim 13, wherein the operations further include:
receiving an alert message from the public social network identity of the hospital, the alert message indicating an estimated wait time for checking-in for the visit;
in response to receiving the alert message, displaying the alert message in the group chat interface of the group conversation between the social network identity of the user and the public social network identity of the hospital.

16. The computer-readable storage medium of claim 13, wherein the operations further include:
receiving description of one or more symptoms from the user in the group chat interface;

sending the description of the one or more symptoms to the public social network identity of the hospital;

receiving instruction from a hospital server to add social network identities of one or more hospital departments to the group conversation; and in response to receiving the instruction from the hospital server, adding the social network identities of the one or more hospital departments to the group conversation.

17. The computer-readable storage medium of claim 13, wherein the operations further include:

displaying social network identities of a plurality of hospital departments associated with the hospital in the group chat interface;

receiving user input selecting one or more of the plurality of hospital departments in the group chat interface; and in response to receiving the user input selecting the one or more of the plurality of hospital departments in the group chat interface:

obtaining respective registration numbers for each of the one or more hospital departments; and adding social network identities of the one or more hospital departments to the group conversation.

\* \* \* \* \*